United States Patent
Armstrong et al.

(10) Patent No.: US 7,489,561 B2
(45) Date of Patent: Feb. 10, 2009

(54) IMPLANTABLE MEDICAL DEVICE WITH RECONFIGURABLE NON-VOLATILE PROGRAM

(75) Inventors: Randolph K. Armstrong, Houston, TX (US); Scott A. Armstrong, Danbury, TX (US)

(73) Assignee: Cyberonics, Inc., Houston, TX (US)

( * ) Notice: Subject to any disclaimer, the term of this patent is extended or adjusted under 35 U.S.C. 154(b) by 619 days.

(21) Appl. No.: 11/257,267

(22) Filed: Oct. 24, 2005

(65) Prior Publication Data
US 2007/0091687 A1    Apr. 26, 2007

(51) Int. Cl.
G11C 11/34 (2006.01)
(52) U.S. Cl. .............................. 365/185.29; 365/185.11
(58) Field of Classification Search ............ 365/185.29, 365/185.11; 607/2
See application file for complete search history.

(56) References Cited

U.S. PATENT DOCUMENTS

| | | |
|---|---|---|
| 4,197,850 A | 4/1980 | Schulman |
| 4,424,812 A | 1/1984 | Lesnick |
| 4,459,989 A | 7/1984 | Borkan |
| 4,606,349 A | 8/1986 | Livingston et al. |
| 4,612,934 A | 9/1986 | Borkan |
| 4,702,254 A | 10/1987 | Zabara |
| 4,712,179 A | 12/1987 | Heimer |
| 4,809,697 A | 3/1989 | Causey, III et al. |
| 4,867,164 A | 9/1989 | Zabara |
| 5,003,975 A | 4/1991 | Hafelfinger et al. |
| 5,025,807 A | 6/1991 | Zabara |
| 5,029,128 A | 7/1991 | Toda |
| 5,080,096 A | 1/1992 | Hooper et al. |
| 5,081,987 A | 1/1992 | Nigam |
| 5,154,172 A | 10/1992 | Terry, Jr. et al. |
| 5,188,104 A | 2/1993 | Wernicke et al. |
| 5,222,494 A | 6/1993 | Baker, Jr. |
| 5,263,480 A | 11/1993 | Wernicke et al. |
| 5,299,569 A | 4/1994 | Wernicke et al. |
| 5,350,414 A | 9/1994 | Kolen |
| 5,354,320 A | 10/1994 | Schaldach et al. |
| 5,360,437 A | 11/1994 | Thompson |

(Continued)

FOREIGN PATENT DOCUMENTS

EP    0402683 B1    2/1998

(Continued)

OTHER PUBLICATIONS

Terry, Reese S.; The Implantable Neurocybernetic Prosthesis System; PACE, vol. 14, 1991; pp. 86-93.

(Continued)

Primary Examiner—Son Dinh
(74) Attorney, Agent, or Firm—Williams, Morgan and Amerson; Timothy L. Scott

(57) ABSTRACT

A device comprises a stimulus generator comprising an instruction processor. The stimulus generator is configured to deliver stimuli to a biological tissue. The device also comprises a non-volatile memory for storing instructions directly executable by the instruction processor, the instructions controlling, at least in part, the operation of the device. The instruction processor generates an erase control signal to erase at least a segment of the non-volatile memory and a write control signal to write one or more new instructions to at least a segment of the non-volatile memory, thereby modifying the operation of the device.

24 Claims, 4 Drawing Sheets

U.S. PATENT DOCUMENTS

| | | | |
|---|---|---|---|
| 5,411,528 A | 5/1995 | Miller et al. |
| 5,411,536 A | 5/1995 | Armstrong |
| 5,423,873 A | 6/1995 | Neubauer et al. |
| 5,443,486 A | 8/1995 | Hrdlicka et al. |
| 5,456,692 A | 10/1995 | Smith, Jr. et al. |
| 5,507,786 A | 4/1996 | Morgan et al. |
| 5,540,734 A | 7/1996 | Zabara |
| 5,558,640 A | 9/1996 | Pfeiler et al. |
| 5,569,186 A | 10/1996 | Lord et al. |
| 5,725,559 A | 3/1998 | Alt et al. |
| 5,792,203 A | 8/1998 | Schroeppel |
| 5,935,099 A | 8/1999 | Peterson et al. |
| 5,941,829 A | 8/1999 | Saltzstein et al. |
| 5,941,906 A | 8/1999 | Barreras, Sr. et al. |
| 6,016,449 A | 1/2000 | Fischell et al. |
| 6,024,539 A | 2/2000 | Blomquist |
| 6,052,624 A | 4/2000 | Mann |
| 6,104,956 A | 8/2000 | Naritoku et al. |
| 6,128,538 A | 10/2000 | Fischell et al. |
| 6,208,894 B1 | 3/2001 | Schulman et al. |
| 6,238,337 B1 | 5/2001 | Kambhatla et al. |
| 6,241,704 B1 | 6/2001 | Peterson et al. |
| 6,270,455 B1 | 8/2001 | Brown |
| 6,282,450 B1 | 8/2001 | Hartlaub et al. |
| 6,308,102 B1 | 10/2001 | Sieracki et al. |
| 6,341,236 B1 | 1/2002 | Osorio et al. |
| 6,418,346 B1 | 7/2002 | Nelson et al. |
| 6,442,433 B1 | 8/2002 | Linberg |
| 6,466,822 B1 | 10/2002 | Pless |
| 6,477,417 B1 | 11/2002 | Levine |
| 6,480,743 B1 | 11/2002 | Kirkpatrick et al. |
| 6,522,928 B2 | 2/2003 | Whitehurst et al. |
| 6,563,734 B2 * | 5/2003 | Taki ............... 365/185.11 |
| 6,587,724 B2 | 7/2003 | Mann |
| 6,587,727 B2 | 7/2003 | Osorio et al. |
| 6,609,031 B1 | 8/2003 | Law et al. |
| 6,622,047 B2 | 9/2003 | Barrett et al. |
| 6,622,048 B1 | 9/2003 | Mann et al. |
| 6,625,492 B2 | 9/2003 | Florio et al. |
| 6,635,014 B2 | 10/2003 | Starkweather et al. |
| 6,662,052 B1 | 12/2003 | Sarwal et al. |
| 6,662,053 B2 | 12/2003 | Borkan |
| 6,671,547 B2 | 12/2003 | Lyster et al. |
| 6,671,556 B2 | 12/2003 | Osorio et al. |
| 6,690,397 B1 | 2/2004 | Daignault, Jr. |
| 6,690,974 B2 | 2/2004 | Archer et al. |
| 6,694,191 B2 | 2/2004 | Starkweather et al. |
| 6,731,986 B2 | 5/2004 | Mann |
| 6,748,276 B1 | 6/2004 | Daignault, Jr. et al. |
| 6,804,558 B2 | 10/2004 | Haller et al. |
| 6,819,956 B2 | 11/2004 | DiLorenzo |
| 6,985,088 B2 | 1/2006 | Goetz et al. |
| 2002/0065509 A1 | 5/2002 | Lebel et al. |
| 2002/0099412 A1 | 7/2002 | Fischell et al. |
| 2003/0095648 A1 | 5/2003 | Kaib et al. |
| 2003/0144711 A1 | 7/2003 | Pless et al. |
| 2003/0236558 A1 | 12/2003 | Whitehurst et al. |
| 2004/0167587 A1 | 8/2004 | Thompson |
| 2004/0210274 A1 | 10/2004 | Bauhahn et al. |
| 2005/0038484 A1 | 2/2005 | Knudson et al. |
| 2005/0049655 A1 | 3/2005 | Boveja et al. |
| 2005/0075681 A1 | 4/2005 | Rezai et al. |
| 2005/0131493 A1 | 6/2005 | Boveja et al. |
| 2005/0131506 A1 | 6/2005 | Rezai et al. |
| 2006/0020292 A1 | 1/2006 | Goetz et al. |
| 2006/0079942 A1 | 4/2006 | Deno et al. |
| 2006/0149184 A1 * | 7/2006 | Soykan et al. ............ 604/20 |

FOREIGN PATENT DOCUMENTS

| | | |
|---|---|---|
| GB | 2026870 A | 2/1980 |
| GB | 2079610 A | 1/1982 |
| WO | 2004036377 A2 | 4/2004 |

OTHER PUBLICATIONS

DeGiorgio, Christopher M.; Vagus Nerve Stimulation: Analysis of Device Parameters in 154 Patients During the Long-Term XE5 Study; Epilepsia, vol. 42, No. 8, 2001; pp. 1017-1020.

Boon, Paul, et al.; Programmed and Magnet-Induced Vagus Nerve Stimulation for Refractory Epilepsy; J. Clin Neurophysical, vol. 18, No. 5, 2001; pp. 402-407.

* cited by examiner

IMPLANTABLE MEDICAL DEVICE WITH RECONFIGURABLE NON-VOLATILE PROGRAM

BACKGROUND

1. Technical Field

The disclosed subject matter relates generally to implantable medical devices and more particularly to reconfigurable non-volatile programming in an implantable medical device.

2. Background Information

Various diseases and disorders of the nervous system are associated with abnormal neural discharge patterns. One treatment regimen for such diseases and disorders includes drug therapy. Another treatment technique includes the implantation in the patient of an implantable medical device that comprises a pulse generator for electrically stimulating a target location of the patient's neural tissue. In one such available treatment for epilepsy, the vagus nerve is electrically stimulated by a neurostimulator device substantially as described in one or more of U.S. Pat. Nos. 4,702,254, 4,867,164, and 5,025,807, all of which are incorporated herein by reference.

Some implantable pulse generators used for electrical stimulation of neurological tissue operate according to a therapy algorithm programmed into the device by a health care provider such as a physician. One or more therapy parameters or the actual software running on the device may thereafter be changed by reprogramming the neurostimulator after implantation by transcutaneous communication between an external programming device and the implanted neurostimulator. The ability to program (and later re-program) the implanted medical device ("IMD") permits a health care provider to customize the therapy provided by the implanted device to the patient's needs, to update the therapy periodically should those needs change, and to update the software of the device, including the operating system.

Various reprogrammable IMDs such as those discussed above are processor-controlled. The processors in such devices execute software loaded into memory contained within the IMD. For program security, various IMDs in the related art use read-only memory ("ROM") or programmable read-only memory ("PROM"). Use of ROM or PROM ensures the security of the programming stored therein. However, when software improvements arise, there is a need for upgrades or modifications to the software stored in the IMD, and ROM and PROM memories have the inherent limitation that they cannot be reprogrammed without physically changing the memory in the IMD, thus necessitating an explant of the IMD.

For these reasons, many IMDs of the related art use re-writable memory (i.e. random-access memory, or "RAM") that enables upgrades and modification to the software, in combination with some form of ROM. Each of the methods currently used in the related art has limitations, as discussed below.

Various IMDs employ volatile RAM, wherein program contents are volatile and subject to loss due to power fluctuations. One limitation of such a design is that loss of power results in an unrecoverable loss of the programming and the therapy parameters stored therein. A further shortcoming of such a design is that when a software program is executed directly from RAM (i.e., without employing virtual memory, pointers and the like), error checking is required for all instructions prior to every execution to prevent execution of an instruction altered by a power fluctuation. The requirement of error checking circuitry adds significant complexity to the IMD system.

Other IMDs of the related art use volatile, programmable RAM for the main program with a program back-up in ROM, wherein program contents in RAM may be lost due to power fluctuations, but upon losing power, the IMD reverts to the non-modifiable back-up program in stored in ROM. One limitation of such a design is the requirement of both a RAM and a ROM of sufficient size to store the executable program. Various designs in the related art have attempted to address this limitation. For example, in one design, the majority of the executable program may be stored in ROM while pointers to the various tasks in ROM are maintained in RAM, backed by Electrically Erasable Programmable Read Only Memory (EEPROM). While such a design minimizes the size of the RAM needed, such an approach also limits the degree of possible upgrade or modification based on the quantity of available RAM and the granularity of the tasks (i.e. the size of individual tasks relative to the code size and execution time). Another related design provides RAM and ROM of similar sizes, and uses a memory mapping system to swap either type of memory into a virtual memory space used by the processor. Such a design does not solve the problem that both the RAM and the ROM must be of sufficient size to store the executable program and the processor cannot directly execute the program. Additionally, a virtual memory design adds undesirable complexity to the IMD.

Various other IMDs employ volatile, programmable RAM backed up by program back-up in non-volatile Ferroelectric RAM ("FRAM"). One limitation of such a design is that both the RAM and the FRAM must be of sufficient size to store the executable program. Also, FRAM suffers from the deficiency that repeated read access of a FRAM location causes the FRAM to lose its non-volatility. Specifically, the physical nature of the crystal employed by FRAM is such that an almost infinite number of writes is possible, but the crystal deteriorates with each read, causing the FRAM to lose its non-volatility after a number of reads (typically in the range of 10 billion reads). The limited non-volatility lifetime of FRAM is particularly problematic for executable programs stored in the FRAM. Such programs often contain execution loops that result in repeated access of the FRAM. For applications such as the execution of software in an IMD, wherein relatively few writes are necessary, but, taking programming loops into account, vast numbers of reads are necessary, FRAM is thus inadequate. Still further, when the program is executed directly from RAM, there is a need for error checking on all instructions prior to execution to prevent execution of an instruction altered by a power fluctuation, adding significant complexity to the IMD system.

Still other IMDs of the related art use volatile, programmable RAM with a program back-up in a Serial Electrically Erasable Programmable ROM ("SEEPROM"). Such a design requires both RAM and SEEPROM of sufficient size to store the executable program. A further shortcoming of such a design is that when programming is executed directly from the RAM, as before, error checking is required for all instructions prior to execution to prevent execution of an instruction altered by a power fluctuation.

It is desirable, therefore, for an IMD, such as a neurostimulator, to be able to upgrade both therapy parameters and operational programming for the device post-manufacture and/or post-implant without the need for 1) large amounts of RAM, 2) ROM or RAM back-up, 3) indirect execution, (e.g., with a virtual memory area, pointers or the like) or 4) instruction error-checking.

BRIEF SUMMARY

In accordance with at least one embodiment, a device comprises an electrical signal generator and a non-volatile memory. The signal generator comprises an instruction processor, and is configured to deliver an electrical signal to a biological tissue. The non-volatile memory is for storing instructions directly executable by the instruction processor, and the instructions control, at least in part, the operation of the device. The instruction processor is capable of generating 1) an erase control signal to erase at least a segment of the non-volatile memory and 2) a write control signal to write one or more new instructions to at least a segment of the non-volatile memory, thereby modifying the operation of the device.

In accordance with at least one embodiment, a medical system comprises an implantable medical device (IMD) configured to deliver stimuli to a biological tissue and an external device capable of non-invasive communication with the IMD. The IMD includes a non-volatile memory for storing instructions directly executable by an instruction processor, the instructions controlling, at least in part, the operation of the IMD, and an IMD telemetry system operable for non-invasive, wireless communication with the external device. The instruction processor, upon a command to update, generates an erase control signal to erase at least a segment of the non-volatile memory and a write control signal to write at least a segment of the non-volatile memory, thereby modifying the operation of the IMD. The external device includes an external device telemetry system operable for non-invasive, wireless communication with the IMD, wherein the external device telemetry system sends one or more new instructions to the IMD telemetry system.

In accordance with at least one embodiment, method of updating an IMD having a non-volatile memory comprises storing a first program in a non-volatile memory. The first program is configured to operate an IMD and is executable by an instruction processor. The method comprises execution of the first program directly from the non-volatile memory. The method further comprises erasing at least a segment of the non-volatile memory and writing a second program to the erased segment of the non-volatile memory. The second program is configured to operate the IMD and is executable by the instruction processor. The method comprises executing the second program directly from the non-volatile memory.

The preferred embodiments described herein do not limit the scope of this disclosure.

Notation and Nomenclature

Certain terms are used throughout the following description and claims to refer to particular system components. As one skilled in the art will appreciate, implant companies may refer to a components or groups of components by different names. This document does not intend to distinguish between components or groups thereof that differ in name but not function. In the following discussion and in the claims, the terms "including" and "comprising" are used in an open-ended fashion, and thus should be interpreted to mean "including, but not limited to . . . ."

Random-Access Memory ("RAM"), as used herein, refers to a memory that permits access to any of its address locations in any desired sequence with similar access time to each location. The term RAM denotes a read/write memory. Additionally, RAM is volatile, meaning that the power is necessary to hold the stored contents and that loss of power results in loss of the stored content of the memory.

Ferroelectric RAM ("FRAM"), as used herein, refers to random access memory that combines the fast read/write access of dynamic RAM (DRAM) with the ability to retain data when power is turned off (as do other non-volatile memory devices such as ROM and flash memory). Due to the physical nature of the FRAM cell (i.e., a crystal having a state altered with each read), however, there is a limit to the number of read accesses it will tolerate before it loses its non-volatility.

Read-Only Memory ("ROM"), as used herein, refers to a type of memory that maintains data though losses of power. In some implementations, ROM may actually be writeable, using vendor-dependent protocols.

Programmable ROM ("PROM"), as used herein, refers to a form of non-volatile memory that is supplied with null contents and is loaded with its contents in the laboratory or in the field. Once programmed, its contents cannot be changed.

Electrically Erasable PROM ("EEPROM"), as used herein, is a reprogrammable read-only memory in which cells may be erased electrically and in which each cell may be reprogrammed electrically.

Flash memory, as used herein, refers to a form of EEPROM that allows multiple memory locations to be erased or written in one programming operation. Flash is a form of rewritable memory chip that, unlike a Random Access Memory chip, holds its contents without maintaining a power supply. One significant difference between Flash and EEPROM is that flash devices are erased one sector at a time, not byte-by-byte as with EEPROM.

BRIEF DESCRIPTION OF THE DRAWINGS

For a more detailed description of the preferred embodiments of the present invention, reference will now be made to the accompanying drawings, wherein.

DETAILED DESCRIPTION OF THE PREFERRED EMBODIMENTS

The present invention is susceptible to implementation in various embodiments. The disclosure of specific embodiments, including preferred embodiments, is not intended to limit the scope of the invention as claimed unless expressly specified. In addition, persons skilled in the art will understand that the invention has broad application. Accordingly, the discussion of particular embodiments is meant only to be exemplary, and does not imply that the scope of the disclosure, including the claims, is limited to specifically disclosed embodiments.

Figure 1:
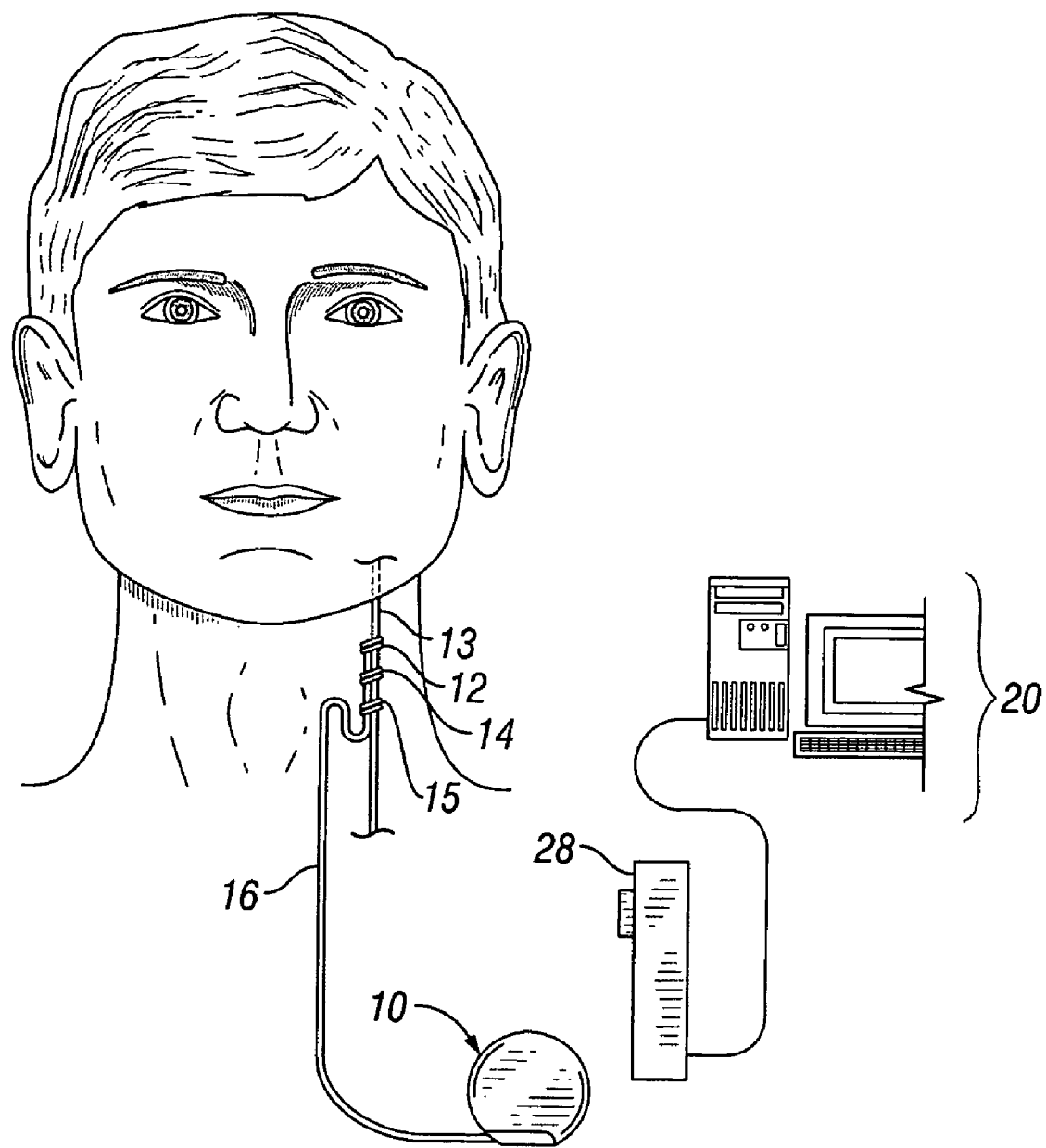
FIG. 1 depicts, in schematic form, an implantable medical device, in accordance with a preferred embodiment of the invention, implanted within a patient and programmable by an external programming system.

FIG. 1 illustrates an implantable medical device ("IMD") 10 implanted in a patient. The IMD 10 may be representative of any of a variety of medical devices. At least one preferred embodiment of the IMD 10 comprises a neurostimulator for stimulating a neural structure in a patient, particularly a neurostimulator for stimulating a patient's cranial nerve such as a vagus nerve 13. Although the IMD 10 is described below in terms of a vagus nerve stimulation ("VNS") embodiment, the disclosure and claims that follow are not limited to VNS, and may be applied to the stimulation of other tissues such as the trigeminal and/or glossopharyngeal nerves, or to other neural tissue such as one or more brain structures of the patient, spinal nerves, and other spinal structures, as well as non-neural tissue and organs. Although the IMD 10 is described in terms of an electrical signal generator for electrical stimulation of neural tissue, the disclosure is applicable to other types of stimulus generators such as chemical infusion pumps and mechanical stimulation devices for providing stimulation modalities other than, or in addition to, electrical stimulation.

Referring still to FIG. 1, a lead assembly 16 comprising one or more leads is coupled to the IMD 10, in the illustrated embodiment an electrical signal generator. The lead assembly 16 includes one or more electrodes, such as electrodes 12 and 14. Each lead assembly 16 has a proximal end that connects to the IMD 10; the electrodes 12,14 are coupled to a distal end. At least one electrode 12 or 14, and preferably an electrode pair (12 and 14), is used as a stimulating electrode to deliver the electrical signal to target tissues such as the patient's vagus nerve 13. At least one electrode 12, 14 (preferably an electrode pair 12 and 14) may in some embodiments be used as a sensing electrode to detect electrical activity of target tissue (e.g., the vagus nerve 13). In alternative embodiments, separate sensing electrode(s) may be used. The housing (or "can") of the IMD 10 may also be used as a stimulating sensing electrode.

Further still, some embodiments include a combination of stimulation-only electrodes, sensing-only electrodes, and combination stimulation and sensing electrodes. The number of stimulation-capable, sensing-capable, and the total number of electrodes can be selected as desired for the given application. Other additional electrodes can function as sensing electrodes to sense any target parameter in the patient's body, such as, for example, a parameter related to the patient's heart, the patient's blood pH, blood pressure, blood sugar, movement of the patient, or other parameters related to the patient's physical condition. Other types of sensors well known in the art may additionally be used to monitor such parameters. Examples of electrodes suitable for coupling to a vagus nerve 13 to provide VNS therapy to a patient are available from Cyberonics, Inc. (Houston, Tex.) as the Model 300 and Model 301 electrodes. Other suitable electrodes are disclosed in U.S. Pat. No. 4,979,511, incorporated herein by reference in its entirety. An anchoring tether 15 is provided in lead assembly 16 to provide strain relief, an example of which is also described in U.S. Pat. No. 4,979,511

FIG. 1 also illustrates an external device implemented as a programming system 20 for the IMD 10. The programming system 20 may comprise a personal computer, personal digital assistant (PDA) device, or other suitable computing device consistent with the description contained herein, as well as a wand 28 used for transmitting and receiving signals to and from the IMD 10. Methods and apparatus for communication between the IMD 10 and an external programming system 20 are known in the art, including telemetry via an RF communication link. Representative techniques for such communication are disclosed in U.S. Pat. Nos. 5,304,206, and 5,235,980, both incorporated herein by reference. As explained below, the IMD 10 includes a transceiver (such as a coil) that permits signals to be communicated wirelessly between the wand 28 and the IMD 10. Via the wand 28, the programming system 20 generally monitors the performance of the IMD 10 and downloads new executable operational programming (i.e., software) and/or therapy parameters into the IMD 10 to alter its operation as desired.

Figure 2:
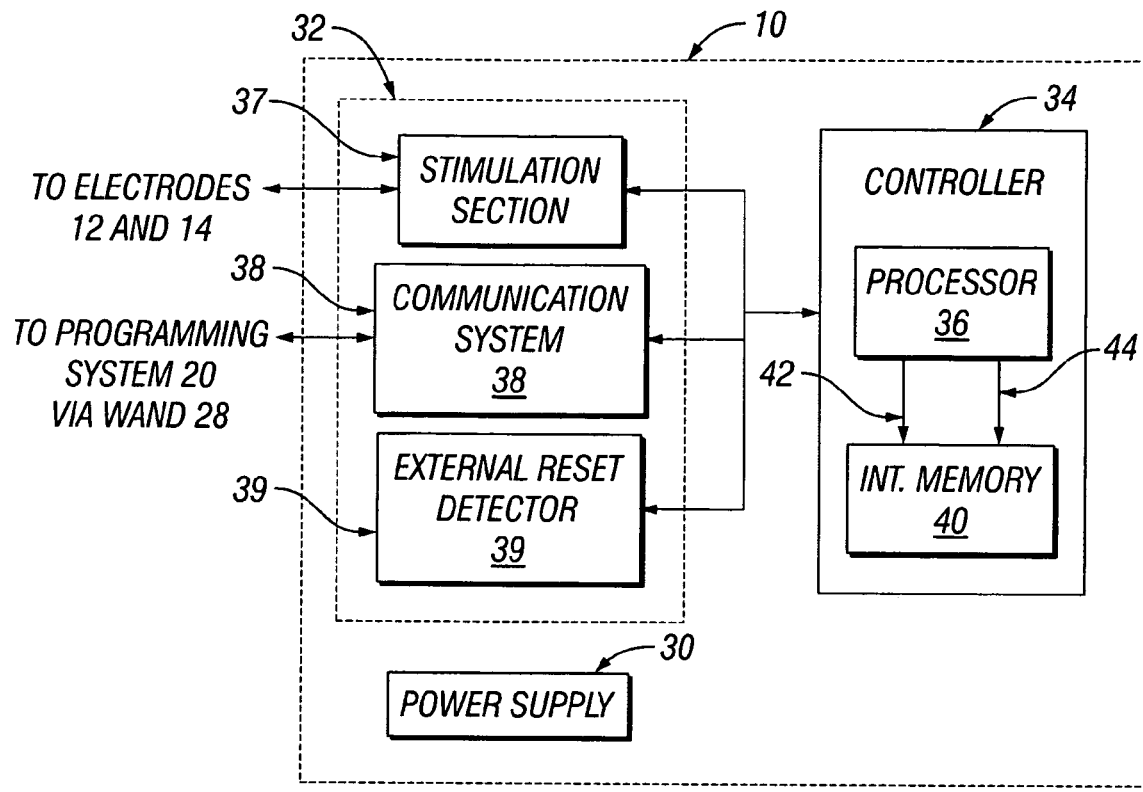
FIG. 2 is a block diagram of the implantable medical device of FIG. 1 and comprising a stimulation and communication unit and a controller.

FIG. 2 shows a block diagram of a preferred embodiment of the IMD 10. As shown, the IMD 10 includes a power supply 30 (e.g., a battery), a stimulation and communication unit ("SCU") 32, and a controller 34. The SCU 32 may comprise, or be referred to as, a "pulse generator" or perform some or all of the functionality of a pulse generator. For example, under the control of controller 34 the stimulation section 37 of the SCU 32 may generate an electrical signal to stimulate a neural structure in a patient. Further, under the control of controller 34 the communication system 38 of the SCU 32 may telemeter data (such as therapy parameters) or operational programming (such as software) to/from the programming system 20 via the wand 28. Further, the SCU 32 may comprise an external reset detector 39, as explained in more detail with respect to FIG. 3. In this embodiment, the battery 30 provides power for both by the SCU 32 and the controller 34. As explained in greater detail with respect to FIG. 3, the SCU 32 includes a voltage regulator 58 that receives voltage from the battery 30 and provides operating voltage for use by the controller 34. In this way, the SCU 32 can control the voltage provided to the controller 34. In an alternative embodiment (shown in FIG. 3) the SCU may also comprise a sensing unit in communication with one or more body parameter sensors for detecting one or more body parameters of interest.

The controller 34 generally assists, controls, and/or programs the SCU 32. Controller 34 preferably comprises a processor 36 such as a low-power, mixed-signal microcontroller. One suitable processor is available from Texas Instruments, Inc., selected from the MSP430F family of processors. Other suitable processors from the PIC1xF family of processors are available from MicroChip Technology. Other suitable processors may be used and/or integrated into the controller 34, although the processor 36 preferably is capable of processing a variety of sensor inputs, uses low power, and operates at a high speed. In general, however, any suitable processor 36 can be used in the controller 34 to implement the functionality performed by the controller 34 as explained herein. It will be appreciated that some features of the controller 34 may also be provided in whole or in part by the SCU 32, and vice versa. Thus, while certain features of the present invention may be described as comprising part of the SCU 32, it is not intended thereby to preclude embodiments in which the features are provided by the controller. Likewise, certain features described herein as comprising part of the controller 34 are not intended to preclude embodiments in which the features comprise part of the SCU 32.

Figure 4:
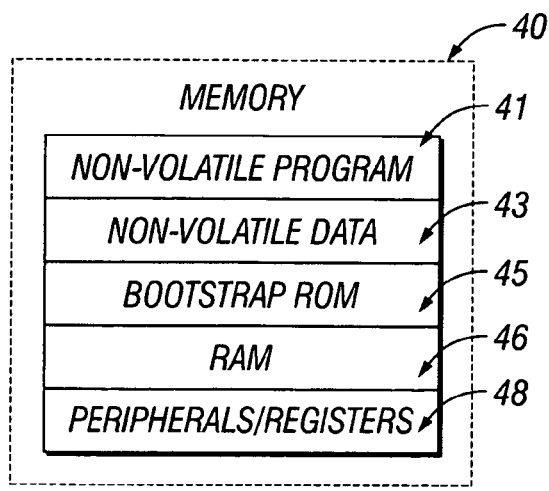
FIG. 4 is a block diagram of the controller memory of the implantable medical device of FIG. 2.

In the embodiment of FIG. 2, the controller 34 additionally comprises a memory 40 integrated into the controller, as explained in greater detail with respect to FIG. 4. The processor 36 of the controller 34 directly executes programs from the integrated memory 40. That is, executable instructions (i.e., operational programming) can be fetched directly from memory 40 for execution by the processor 36 without first copying the instructions to another memory (e.g., a RAM). The integrated memory 40 may be upgraded by erasing one or more segments of the integrated memory 40 and, via the programmer 20, writing a new program to the integrated memory 40. Among other functions, in operation, the processor 36 generates an erase control signal 42 and a write control signal 44 that operate on the memory 40.

Figure 3:
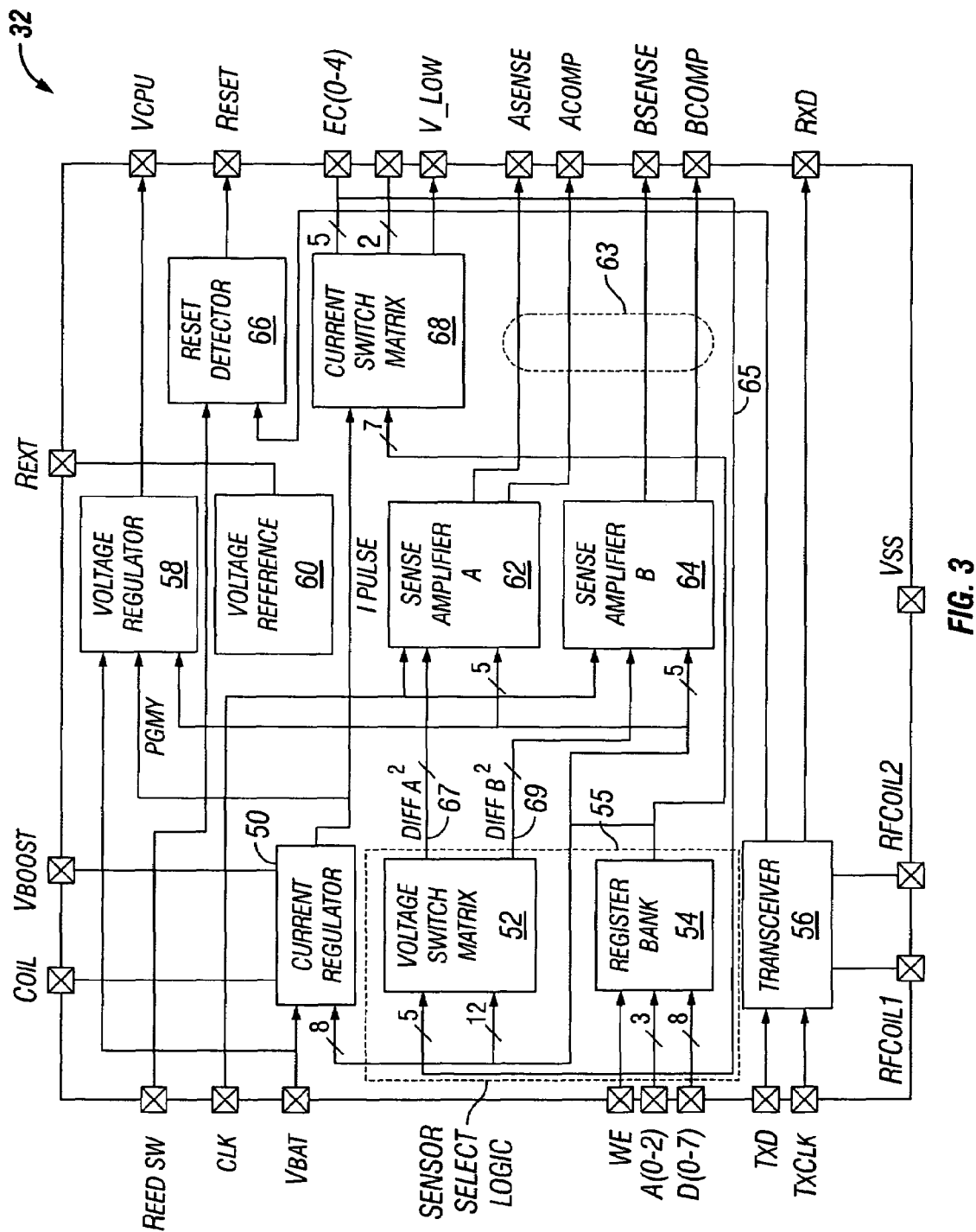
FIG. 3 is a block diagram of the stimulation and communication unit of FIG. 2.

FIG. 3 is a block diagram showing one embodiment of the SCU 32 depicted in FIG. 2. Although a particular architecture for SCU 32 is provided in FIG. 3, the recitation of a particular architecture is not intended to limit the scope of the invention, which is limited only by the claims. The SCU 32 comprises a current regulator 50, a voltage switch matrix 52, a register bank 54, a transceiver 56, a voltage regulator 58 (previously noted), a voltage reference 60, a pair of sense amplifiers 62 and 64, a reset detector 66, and a current switch matrix 68. The aforementioned components preferably are coupled together on a single integrated circuit chip as shown, but may also be implemented with other suitable architectures, including individual components or modules, although in general, integration of the components in a small number of modules increases reliability and reduces cost.

In accordance with the embodiment of FIG. 3, the register bank 54 comprises eight control registers. Each register includes eight bits, and the function performed by each register in the FIG. 3 embodiment is described below in Table I. The control registers are generally readable and writeable by the controller 34 (FIG. 2) to control the operation of the SCU 32. Control information provided by the controller 34 to the SCU 32 over the eight data lines (shown in FIG. 3 as "D[0-7]") is latched, upon detection of a rising edge of the write enable ("WE") signal, into the eight bits of the particular SCU register that corresponds to the address provided on the three address signals ("A[0-2]"). Thus, the controller 34 is used to program the registers in the register bank 54 by providing data to be written on the data lines D0-D7, an address corresponding to the target register on the address lines A0-A2, and then asserting the WE signal to cause the target register to be programmed. In this embodiment, each of the eight registers is individually programmable by this process. The register bank 54 also converts the register data received from the controller 34 into one or more digital signals that are used by other components within the SCU 32 as explained in greater detail below.

The eight registers of the register bank 54 are described below in Table I for one embodiment of the present invention.

TABLE I

REGISTER DESCRIPTIONS

| Register Name | General Description |
| --- | --- |
| General Control | Controls the reset for the SCU 32, bandgap trim for the sense amplifiers 62, 64 and trims for other functions |
| Voltage Control | Enables and controls the amount of voltage boost (50) for current control, controls controller power voltage (58) |
| Current Level | Controls the current output level (50) |
| Current Direction | Designates which electrodes function as cathode and anode for current pulse delivery (68), enables electrode discharge and reed switch bypass |
| Sense A Control | Controls operation of sense amp A (62) |
| Sense B Control | Controls operation of sense amp B (64) |
| Sense A Select | Selects positive and negative electrodes via switch matrix 52 for sense amp A (62) |
| Sense B Select | Selects positive and negative electrodes via switch matrix 52 for sense amp B (64) |

In certain preferred embodiments, the IMD 10 provides enhanced energy conservation by enabling two modes of operation for controller 34: a fully operational mode of operation and a lower power, standby mode to conserve battery power. In the fully operational mode of operation, the controller 34 preferably performs some, or all, of the functions described herein. In the standby mode, the controller 34 generally performs fewer functions than in the fully operational mode. In some embodiments, other than refreshing or updating the internal memory contained in the controller, the standby mode generally limits the controller to wait for a transition to the fully operational mode. Because the controller is generally idle in the standby mode, battery power is conserved.

The processor 36 preferably includes an on-chip memory 40, as shown in greater detail in FIG. 4. The memory 40 preferably comprises a non-volatile, re-programmable memory 41 such as flash memory or EEPROM memory that preferably stores the software to be executed by the processor 36 as well as therapy parameters used by the processor 36 in conjunction with the software. The software to be executed and therapy parameters may be stored in combined non-volatile memory or in separate non-volatile memory as shown in FIG. 4, wherein the software to be executed is stored in non-volatile program memory 41 and therapy parameters are stored in non-volatile data memory 43. The voltage required for the controller 34 to re-program its flash memory (via the erase control signal 42 and write control signal 44) may be different than the voltage needed for the controller during other aspects of its operation. The voltage regulator 58 (FIG. 3) in the SCU 32 receives voltage from the battery 30 and provides supply voltage for the controller 34 in its fully operational and standby modes of operation, as well as for programming non-volatile memory contained in the processor 36.

The transceiver 56 (FIG. 3) enables the external wand 28 (FIG. 1) to communicate with the IMD 10. More particularly, in certain embodiments, transceiver 56 permits the external programming system 20 to program the IMD 10 (i.e., send therapy parameters or operational programming to the IMD 10) and to monitor its configuration and state (i.e., query and receive signals from the IMD 10). In addition, transceiver 56 also permits the external programming system 20 (or the patient alone by a suitable signaling means such as a magnet) to inform the implantable IMD 10 of the occurrence of a physiological event such as a seizure.

In one embodiment, the SCU 32 and the controller 34 preferably are reset on initial power-on or if the IMD simultaneously detects both a magnetic field and an RF transmission. Whenever the external reset detector 66, which may comprise, e.g., a Reed switch, in the IMD 10, detects a magnetic field, all current switches in the current matrix 68 of the IMD 10 are turned off as a safety precaution. This safety precaution can be temporarily overridden (i.e., the IMD 10 may continue to generate and deliver electrical pulses to stimulating electrode 14) by writing an override bit in the Current Direction register (listed in Table I). To protect against a "stuck at override" failure, the aforementioned override bit preferably resets itself after triggering an override time interval implemented by the reset detector 66.

Referring to FIG. 4, the integrated memory 40 is shown as comprising memory elements of different types. In one preferred embodiment, the integrated memory 40 is memory that is integrated within the processor 36, though in various other embodiments, the integrated memory 40 may be a separate component that is electrically coupled to the processor 36. In a particular embodiment, shown in FIG. 4, the integrated memory 40 comprises non-volatile program memory 41, non-volatile data memory 43, Bootstrap ROM 45, RAM 46, and Peripherals/Registers memory 48, each of which may be an individual memory device, or which may be present together in integrated circuitry.

The Bootstrap ROM 45 may be utilized to load an initial program into the non-volatile program memory 41 during manufacture. After the initial programming is complete, the Bootstrap ROM 45 may no longer be needed or used for loading programming.

Both the non-volatile program memory 41 and the non-volatile data memory 43 may comprise either Flash memory or EEPROM. Additionally, one or more segments of the non-volatile program memory 41 may be erased at a time. In addition to the IMD program that it contains, the non-volatile program memory 41 may, for additional security, contain a known secure program. In one embodiment, the known secure program may be run initially on reset to provide the ability to reload a new program even if the main program has been corrupted or has a significant error in it. The non-volatile data memory 43 may contain therapy parameters that may be programmed or modified at any time by a healthcare provider such as a physician by way of the wand 28 and the programming system 20. Such programmable therapy parameters may include current, pulse width, pulse frequency, on-time and off-time, according to the nature of the medical treatment and the condition of the patient receiving the treatment.

The controller 34 may use a variable-size portion of the RAM 46 as a temporary "stack" to store information during interrupts or function calls. The controller 34 resumes operation after interrupts or functions using the data it had stored on this stack. Additionally, a fixed-size portion of the RAM 46 may be used by the software program to store temporary variables. One example of such data is values involved in an intermediate calculation. Finally, the software program may use a fixed-size portion of the RAM 46 to store dynamic data, i.e., data that changes frequently and thus does not need to be stored in a non-volatile manner. One example of such data is an elapsed operation time counter.

The portion of the memory 40 dedicated to peripherals and registers 48 stores the control information as described with reference to FIG. 3.

Generally, one method for updating or reprogramming an implantable device proceeds as follows. The implantable device contains a known, secure program that executes as the default program in case of a system reset, and in the situation when no other program is available. Upon reset, the known, secure program begins to run, executed directly from the non-volatile memory where it is stored, using therapy parameters set for default. If the implantable device receives a command from the programmer to load new programming, new programming is loaded into at least a segment of the non-volatile memory. Then the implantable device stops executing the known secure program as the default, and instead the system begins to execute the new programming directly from the non-volatile memory. If a system reset occurs, the known secure program begins to execute. If there is no "load new program" command from the programmer for a certain period of time, the system may run an available program stored in the non-volatile memory. When there is no other available program, the system may revert to the default: the known, secure program. The system will continuously check for whether the programmer has sent a command to load a new program.

Figure 5:
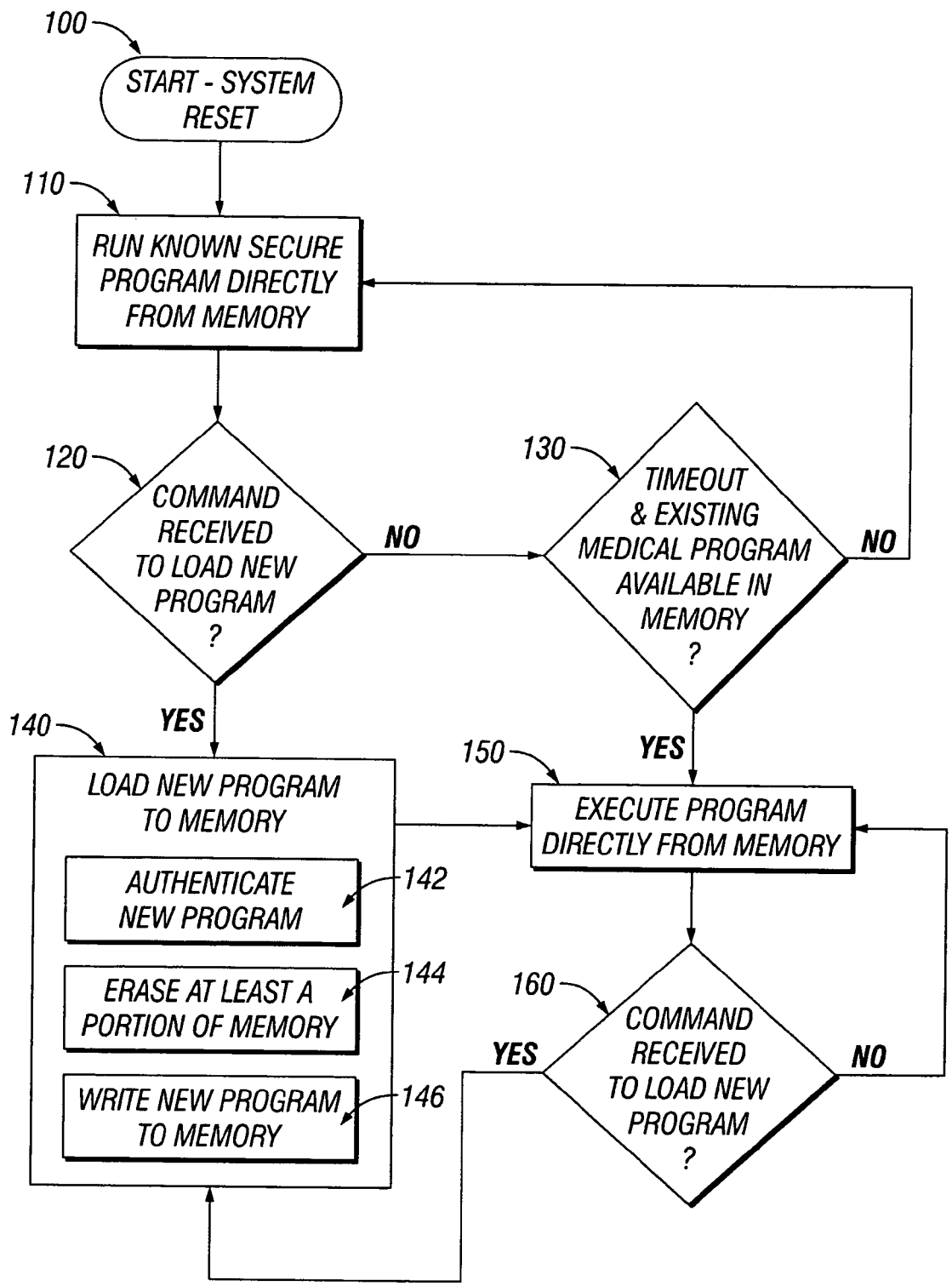
FIG. 5 is a flow chart depicting an exemplary method for updating the software or therapy parameters, in accordance with embodiments of the present invention.

Referring to FIG. 5, a flow chart depicting an exemplary method for updating the software or therapy parameters, in accordance with embodiments of the present invention, is shown. The exemplary method begins with a system reset 100. A system reset may not occur in normal operation, however, an internal error may cause such a reset, or a reset may be executed by command to facilitate a software upgrade. Such a forced reset may be intentionally caused, for example, by a physician.

Upon system reset, the processor 36 begins to run a known secure program directly from the non-volatile program memory 41 (block 110). The known secure program may be limited to an upload program that will enable loading a new executable program (i.e., from the external programming system 20) or reloading of executable programming if the programming already stored in memory has been corrupted. The known secure program may provide limited therapeutic activity or no therapeutic activity at all. Alternatively, the known secure program may be a basic secure program to provide certain therapeutic functions. The known secure program is known to be safe and uncorrupted.

While running the known secure program, the processor 36 checks to see if the programming system 20 has sent a command (via the wand 28) indicating that a new executable program is to be loaded (from the programming system 20, via the wand 28) to memory 40 to run instead of the known secure program (block 120). If the programming system 20 has sent a command indicating that a new executable program is to be loaded, then a new executable program is loaded into the non-volatile program memory 41 (block 140). The new executable program is passed from the programming system 20 via the wand 28 to the communication system 38 of the IMD 10, where it is passed to the controller 34 for storage in the integrated memory 40.

The processor 36 may be configured to error check the new program before storing the new program in non-volatile program memory 41 (block 142). The risk mitigated by error checking is the corruption of data during communication. If communication errors (such as communication noise) were to corrupt the data transferred, the IMD 10 may operate based upon this errant data. If the data were the operational code, the generator may perform an unexpected operation or crash. One exemplary error checking algorithm is known as Cyclic Redundancy Check ("CRC"), which adds prescribed redundant data according to a mathematical protocol. The processor 36 would receive the data as well as the CRC. Using the same mathematical protocol, the processor 36 would use the CRC to identify whether a communication error occurred. CRCs are known in the art and commonly used because they provide significant error detection with very little additional redundant data. In one embodiment, the processor 36 authenticates the new program before erasing or writing the memory 40, thus ensuring that the memory 40 continuously contains a functional program.

Referring again to FIG. 5, loading the new executable program in the non-volatile program memory (block 140) further comprises erasing a segment of the non-volatile program memory by generating an erase control signal 42 (block 144). Loading the new executable program in the non-volatile program memory further comprises writing the new executable program to a segment of the non-volatile program memory by generating a write control signal 44 (block 146). The segment so erased or written to may comprise some or all of the non-volatile memory. Once stored in the integrated memory 40 (specifically, the non-volatile program memory 41), the processor 36 runs the new executable program directly from the non-volatile program memory 41 (block 150).

Additionally in this exemplary method, while running the known secure program, a time-out timer begins to run if the processor 36 does not detect that the programming system 20 has sent a command to load a new executable program. Upon expiration of the time-out timer (e.g., after 15 seconds), if there is an existing executable program available in the non-volatile program memory 41 (block 130), the processor 36 executes the existing executable program directly from the non-volatile program memory 41 (block 150). If there is not an existing executable program available in the non-volatile memory 41 upon expiration of the time-out timer, then the processor 36 executes the known secure program directly from integrated memory 40 (block 110).

While the processor 36 executes the available medical program directly from memory (block 150), the processor 36 continues to check for a command from the external programming system 20 indicating that a new executable program is to be loaded (block 160). If the programming system 20 has sent a command indicating that a new executable program is to be loaded, then a new executable program is loaded into the non-volatile program memory 41 (block 140) and the processor 36 may execute the new executable program directly from the non-volatile program memory 41 (150). If the programming system 20 has not sent such a command, the processor 36 may continue to execute the existing executable program already available in integrated memory 40 directly from integrated memory 40 (block 150), periodically checking for a command from the programming system 20. This continuous loop may continue, running either the existing executable program directly from memory, or loading and then running new executable programming directly from memory, until another system reset occurs.

While preferred embodiments of the present invention have been shown and described, modifications thereof can be made by persons skilled in the art without departing from the spirit and teachings of the invention. The embodiments described herein are exemplary only, and are not intended to limit the scope of protection provided herein.

What is claimed is:

1. A device, comprising:
   an electrical signal generator comprising an instruction processor, the signal generator configured to deliver stimuli to a biological tissue;
   a non-volatile memory for storing instructions that are directly executable by the instruction processor, and that control, at least in part, the operation of the device;
   wherein the instruction processor comprises an instruction erase control signal to erase at least a segment of the non-volatile memory and an instruction write control signal to write one or more new instructions to the erased segment of the non-volatile memory, thereby modifying the operation of the device.

2. The device of claim 1 wherein the non-volatile memory comprises Flash memory.

3. The device of claim 1 wherein the non-volatile memory comprises EEPROM.

4. The device of claim 1 wherein the non-volatile memory is integrated with the instruction processor.

5. The device of claim 1 further comprising error checking logic configured to securely authenticate the one or more new instructions before generation of the erase control signal or the write control signal.

6. The device of claim 1, wherein the non-volatile memory is further operable for storing one or more therapy parameters, and wherein the instruction processor further comprises a data erase control signal to erase at least a segment of the non-volatile memory and a data write control signal to write one or more new therapy parameters to the erased segment of non-volatile memory, thereby modifying the therapy delivered by the device.

7. A medical system, comprising:
   an implantable medical device (IMD) configured to deliver stimuli to a biological tissue, the IMD comprising:
      an instruction processor;
      a non-volatile memory accessible by the instruction processor, the non-volatile memory comprising stored instructions that are directly executable from the non-volatile memory by the instruction processor and which control, at least in part, the operation of the IMD;
      an IMD telemetry system operable for non-invasive, wireless communication with an external device;
      wherein the instruction processor, upon a command to update, generates an erase control signal to erase at least a segment of the non-volatile memory and a write control signal to write one or more new instructions to the erased segment of the non-volatile memory, thereby modifying the operation of the IMD; and
   the system also comprising:
   an external device comprising an external device telemetry system operable for non-invasive wireless communication of one or more new instructions to the IMD telemetry system.

8. The system of claim 7 wherein the non-volatile memory comprises Flash memory.

9. The system of claim 7 wherein the non-volatile memory comprises EEPROM.

10. The system of claim 7 wherein the non-volatile memory is integrated with the instruction processor.

11. The system of claim 7 further comprising error correction logic configured to securely authenticate the one or more new instructions sent by the external device before generation of the erase control signal or the write control signal.

12. A method of updating an implantable medical device (IMD) having a non-volatile memory, comprising:
   writing a first program executable by an instruction processor and configured to operate the IMD in a non-volatile memory;
   executing the first program directly from the non-volatile memory;
   erasing at least a segment of the non-volatile memory;
   writing a second program executable by the instruction processor and configured to operate the IMD to the erased segment of the non-volatile memory; and
   executing the second program directly from the non-volatile memory.

13. The method of claim 12 further comprising resetting the IMD to trigger said erasing and writing.

14. The method of claim 12 wherein erasing the segment of the non-volatile memory comprises generating an erase control signal by the instruction processor.

15. The method of claim 14 wherein erasing the segment of the non-volatile memory comprises receiving a command from a programmer to generate the erase control signal by the instruction processor.

16. The method of claim 12 wherein writing the second program to the erased segment of the non-volatile memory comprises generating a write control signal by the instruction processor.

17. The method of claim 16 wherein writing the second program to the erased segment of the non-volatile memory comprises receiving a command from a programmer to generate the write control signal by the instruction processor.

18. The method of claim 12 further comprising error checking the second program.

19. The method of claim 18, wherein error checking comprises running a CRC algorithm.

20. The method of claim 12 wherein writing the first program in the non-volatile memory comprises writing the first program in Flash memory.

21. The method of claim 12 wherein writing the first program in the non-volatile memory comprises storing the first program in EEPROM.

22. The method of claim 12 wherein writing the second program to the erased segment of the non-volatile memory further comprises writing the second program in Flash memory.

23. The method of claim 12 wherein writing a second program to the erased segment of the non-volatile memory further comprises writing the second program in EEPROM.

24. The method of claim 12 further comprising:
writing one or more therapy parameters, used by a program configured to operate the IMD and executable by the instruction processor, in a non-volatile memory;
erasing a segment of the non-volatile memory; and
writing at least one new therapy parameter to the erased segment of the non-volatile memory, the new therapy parameters being used by the program executable by the instruction processor, thereby altering the therapy delivered.

* * * * *